US00PP35634P3

(12) United States Plant Patent
Werner et al.

(10) Patent No.: US PP35,634 P3
(45) Date of Patent: Feb. 6, 2024

(54) ***CERCIS* PLANT NAMED 'NC2017-9'**

(50) Latin Name: *Cercis canadensis*
Varietal Denomination: NC2017-9

(71) Applicant: North Carolina State University, Raleigh, NC (US)

(72) Inventors: Dennis Werner, Raleigh, NC (US); Leanne M. Kenealy, Durham, NC (US)

(73) Assignee: North Carolina State University, Raleigh, NC (US)

( * ) Notice: Subject to any disclaimer, the term of this patent is extended or adjusted under 35 U.S.C. 154(b) by 180 days.

(21) Appl. No.: 17/968,196

(22) Filed: Oct. 18, 2022

(65) Prior Publication Data

US 2023/0125066 P1 Apr. 20, 2023

Related U.S. Application Data

(60) Provisional application No. 63/257,391, filed on Oct. 19, 2021.

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
See application file for complete search history.

(56) References Cited

U.S. PATENT DOCUMENTS

| | | | |
|---|---|---|---|
| PP10,328 | P | 4/1998 | Covey |
| PP17,161 | P3 | 10/2006 | Woody |
| PP22,097 | P3 | 8/2011 | Werner |

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of *Cercis* plant, referred to by its cultivar name 'NC2017-9', is disclosed. The new variety is characterized by its purple-colored flowers, small and green colored foliage which exhibits an attractive moderate reddish orange color on newly emerging leaves, and moderately slow growing, profuse branching, weeping, and compact growth habit.

2 Drawing Sheets

Figure 1:
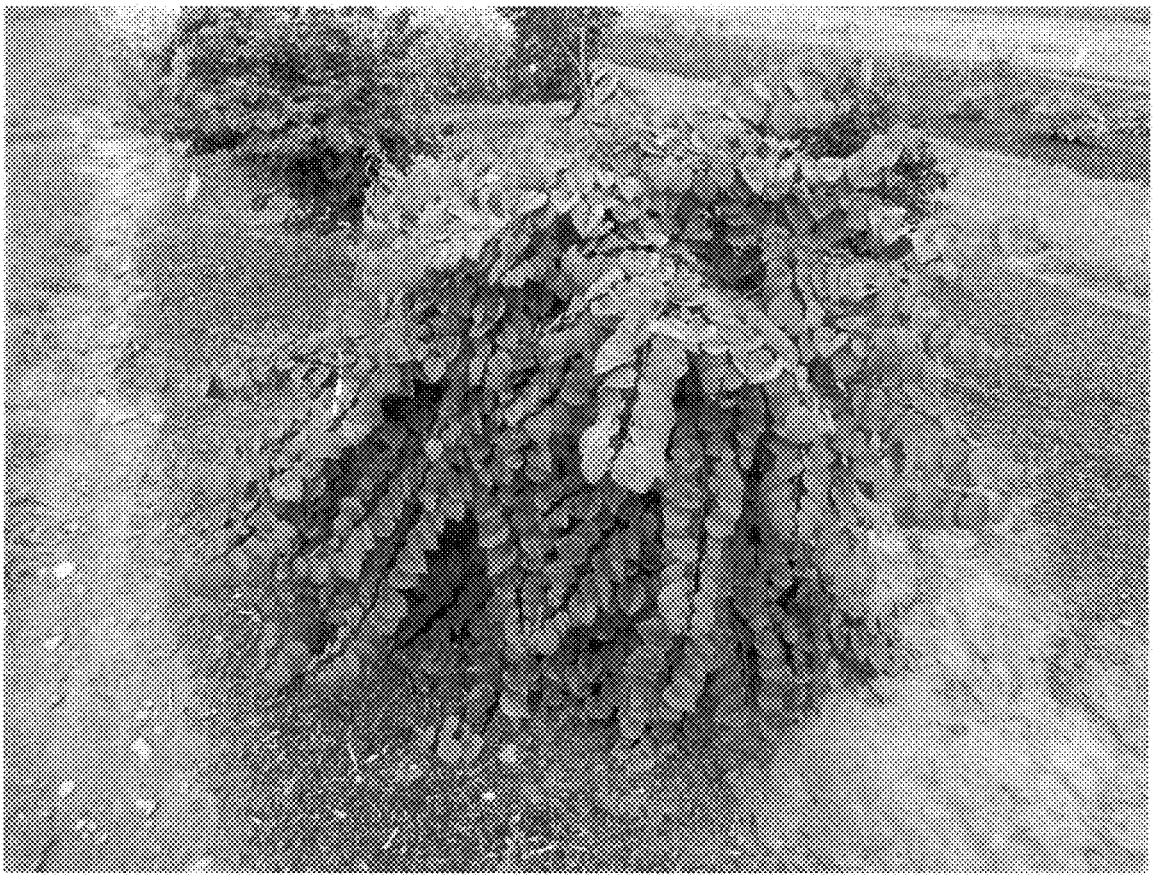

Latin name of genus and species of plant claimed: *Cercis canadensis.*

Variety denomination: 'NC2017-9'.

BACKGROUND OF THE INVENTION

The present invention relates to a new and distinct cultivar of *Cercis* plant botanically known as *Cercis canadensis* and hereinafter referred to by the cultivar name 'NC2017-9'.

The new cultivar originated in a controlled breeding program in Jackson Springs, North Carolina in 2011.

The new *Cercis* cultivar is the result of a controlled cross wherein two parents were crossed which previously had been studied in the hope that they would contribute the desired characteristics. The female parent (i.e., the seed parent) of the new cultivar is *Cercis* 'Ruby Falls', U.S. Plant Pat. No. 22,097. The male parent (i.e., the pollen parent) of the new cultivar is *Cercis* 'Ace of Hearts', U.S. Plant Pat. No. 17,161.

The parentage of the new variety can be summarized as follows:

'Ruby Falls' x 'Ace of Hearts'

The seeds resulting from the above pollination were sown and small plants were obtained which were physically and biologically different from each other. Selective study in 2017 in a controlled environment in Jackson Springs, North Carolina resulted in the identification of a single plant of the new variety, which was selected for its purple-colored flowers, small and green-colored foliage which exhibits an attractive moderate reddish orange color on newly emerging leaves, and moderately slow growing, profuse branching, weeping, and compact growth habit Asexual reproduction of the new cultivar by chip budding since 2017 in Belvidere, Tennessee has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'NC2017-9' as a new and distinct cultivar of *Cercis* plant:

(a) Purple-colored flowers,
(b) Small, green-colored foliage which exhibits an attractive moderate reddish orange color on newly emerging leaves; and
(c) Moderately slow growing, profuse branching, weeping and compact growth habit.

The new variety of the present invention can readily be distinguished from its ancestors. More specifically, plants of 'Ruby Falls' (i.e., the seed parent) display deep purple colored foliage which transitions to burgundy and eventually finishes green during the growing season, whereas plants of the new variety displays green-colored foliage which exhibits an attractive moderate reddish orange color on newly emerging leaves; also plants of the new cultivar have a more open to spreading weeping growth habit compared to the seed parent. In addition, plants of 'Ace of Hearts' (i.e., the pollen parent) exhibit a compact habit, whereas plants of the new variety exhibit a weeping growth habit.

Moreover, the new variety can be readily distinguished from other similar non-parental varieties. Of the many commercially available *Cercis* cultivars, the most similar in comparison to the new cultivar is 'Covey', U.S. Plant Pat. No. 10,328. However, plants of the new cultivar differ from plants of 'Covey' in at least the following characteristics:

1. Plants of the new cultivar are more compact than plants of 'Covey'.
2. Plants of the new cultivar have a smaller leaf size than plants of 'Covey'.
3. Plants of the new cultivar have a shorter internode length than plants of 'Covey'.

BRIEF DESCRIPTION OF THE PHOTOGRAPH

The accompanying photographs show, as nearly true as it is reasonably possible to make the same in color illustrations of this type the typical growth habit of the new cultivar. Colors in the photographs differ slightly from the color values cited in the detailed description, which accurately describes the colors of 'NC2017-9'. The plants in the photographs were approximately four years old and were growing in a test field in Cochranville, PA.

FIG. 1—illustrates a side view of 'NC2017-9'.

Figure 2:
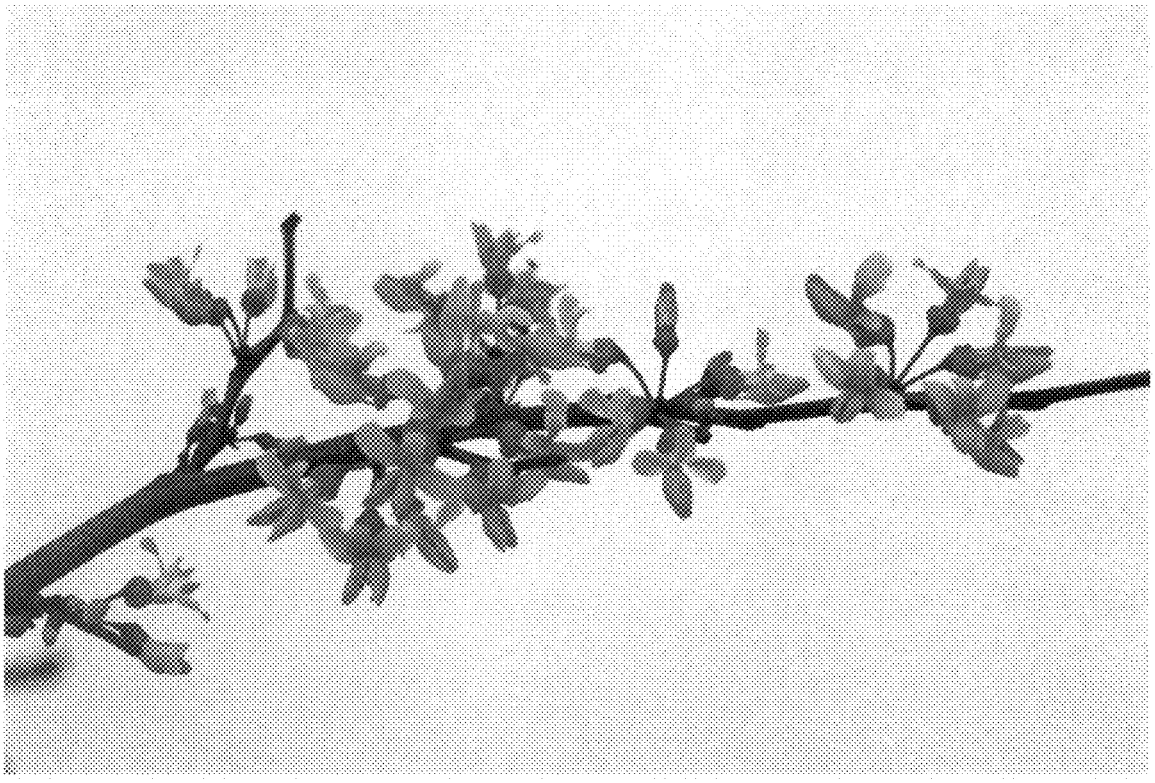

FIG. 2—illustrates flowers at bloom before leafing out.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used.

The following descriptions and measurements describe plants produced from chip budding and grown outside in Jackson Springs, North Carolina. Plants were approximately four years of age. Measurements and numerical values represent averages of typical plants.

Botanical classification: *Cercis canadensis* cultivar NC2017-9.

Parentage:

*Female parent.*—*Cercis* 'Ruby Falls', U.S. Plant Pat. No. 22,097.

*Male parent.*—*Cercis* 'Ace of Hearts', U.S. Plant Pat. No. 17,161.

Propagation:

*Type.*—Chip budding.

Plant description:

*Type.*—Deciduous perennial tree.

*Growth habit and general appearance.*—Moderately slow growing, weeping, compact tree.

*Commercial crop time.*—Approximately 1.5 years from budding to finish as a 2 to 3-foot tree.

*Hardiness.*—USDA Zone 6b.

*Size.*—Height of 4-year-old tree: Approximately 2.3 meters. Width: Approximately 2.2 meters.

*Trunk.*—Texture: slightly rough. Color: 201B.

*Branches.*—Densely branched. Branching habit: multi-branching, weeping architecture. Strength: Moderately strong. Diameter of one-year old growth: Approximately 5.0 mm. Stem Length of one-year old shoots: 51.0 cm. Internode length: 1.4 cm on average. Stem Shape: Circular. Growth pattern: slightly zigzag, deviating less than 5 degrees from vertical at each node. Texture of new growth: Slightly rugose. Color of young stem: 177B. Color of mature stem: previous seasons growth is N200B. Lenticel: numerous, tiny. Lenticel length: 1.0 mm or less. Lenticel shape: circular to slightly elongate. Lenticel color: 197C.

Foliage description:

*General description.*—Type: Deciduous. Arrangement: Alternate.

*Leaves.*—Shape of mature leaves: Cordate. Apex: Distinctly pointed. Base: Cordate. Margin: Entire. Length to base of sinus: Approximately 3.8 cm. Length to end of lobe: Approximately 4.6 cm. Sinus indentation: Approximately 0.8 cm. Width: Approximately 4.1 cm. Texture of upper and lower surfaces: Slightly rugose. Venation pattern: Reticulate. Color of upper surface of immature foliage: 178C with indistinguishable venation. Color of lower surface of immature foliage: 174A with indistinguishable venation. Color of upper surface of mature foliage: 137B with indistinguishable venation. Color of lower surface of mature foliage: 147B with indistinguishable venation. Fragrance: None detected.

*Petiole.*—Length: Approximately 2.4 cm. Diameter: Approximately 1.0 mm. Texture: Smooth, glabrous. Color: 166A.

Flowering description:

*Flowering season.*—Flowers in early spring for about 2-3 weeks depending on weather conditions.

*General description.*—Form: Fasicle. Flower Arrangement: Sessile clusters. Symmetry: Bilateral symmetry. Type: Papilionaceous. Quantity per cluster: 6 per cluster on average. Flower length: 7.0 mm on average. Flower width across wings at anthesis: 5.0 mm on average. Flower depth (bottom of keel petals to top of wings): 5.0 mm on average.

*Bud just before opening.*—Shape: slightly elongate. Diameter: Approximately 1.0 mm. Length: Approximately 1.0 mm. Color: 60A. Texture: Glabrous.

*Petals.*—Quantity: 5, unfused. Texture of upper and lower surfaces: Glabrous. Color when first open: 65B. Color when fully open: 72C.

*Calyx.*—Shape: vase-shaped. Diameter: Approximately 3.0 mm at top of hypanthium. Length: Approximately 2.0 mm. Color of outer and inner surfaces: 59C. Texture of inner and outer surfaces: Glabrous.

*Sepals.*—Arrangement: Fused.

*Pedicel.*—Strength: Strong. Shape: Round. Length: Approximately 0.4 cm. Diameter: Less than 1.0 mm. Texture: Glabrous. Color: 60C.

*Reproductive organs.*—Androecium: Stamen quantity per flower: 10 on average, unfused. Stamen length: 5.0 mm. Stamen width: Less than 1.0 mm. Anther shape: Round. Anther color: 59D. Filament length: 5.0 mm. Filament width: Less than 1.0 mm. Filament color: 59C. Pollen amount: Sparse. Pollen color: 11B. Gynoecium: Pistil length: Approximately 5.0 mm on average. Pistil width: Less than 1.0 mm. Pistil texture: Glabrous. Stigma shape: Round. Stigma color: 59C. Stigma length: Less than 1.0 mm. Stigma width: Less than 1.0 mm. Style shape: round. Style width: Less than 1.0 mm. Style color: 59C. Ovary position: Superior. Ovary shape: Elongate. Ovary length: Less than 1.0 mm. Ovary width: Less than 1.0 mm. Ovary color: 59A.

*Seed production.*—None observed to date.

*Disease and pest resistance.*—Plants of the new *Cercis* have not been noted to be resistant to pathogens and pests common to *Cercis*.

We claim:

1. A new and distinct cultivar of *Cercis* plant named 'NC2017-9', substantially as herein illustrated and described.

* * * * *